United States Patent [19]

Jones

[11] 4,192,611
[45] Mar. 11, 1980

[54] REFLECTIVITY COMPENSATING APPARATUS

[75] Inventor: Horace T. Jones, Rockville, Md.

[73] Assignee: Baxter Travenol Laboratories, Inc., Deerfield, Ill.

[21] Appl. No.: 886,284

[22] Filed: Mar. 13, 1978

[51] Int. Cl.$^2$ .............................................. G01J 3/42
[52] U.S. Cl. .................................... 356/320; 356/325
[58] Field of Search ................ 356/320, 323, 324, 325

[56] References Cited

U.S. PATENT DOCUMENTS

| | | | |
|---|---|---|---|
| 3,436,541 | 4/1969 | Boronkay | 356/325 |
| 3,658,422 | 4/1972 | Wilkinson | 356/323 |
| 3,787,121 | 1/1974 | Lowy et al. | 356/73 |
| 3,986,776 | 10/1976 | George | 356/323 |

Primary Examiner—Vincent P. McGraw
Attorney, Agent, or Firm—Henry W. Collins; Paul Flattery; Thomas Vigil

[57] ABSTRACT

The reflectivity compensating apparatus is utilized in a dual wavelength spectrophotometer wherein a chopper mirror, having alternating mirror segments and open spaces equal in area, cuts through a light beam from a light source and the mirror segments reflect light through a liquid sample in a sample container to a photodetector having an output channel. The reflectivity of each mirror segment varies slightly from the other segments. The compensating apparatus includes a plurality of impedances each of which is related to the reflectivity of a particular mirror segment, a control circuit including a sensing device for sensing which mirror segment is reflecting light and a switch circuit responsive to the output signal from the control circuit to couple a particular impedance to the output signal channel, the particular impedance being related to the reflectivity of the mirror segment which is then reflecting light and generating the signal appearing on the output signal channel thereby to attenuate the output signal to a base line signal level so that the output signal is essentially independent of and not affected by the different reflectivities of the mirror segments.

7 Claims, 3 Drawing Figures

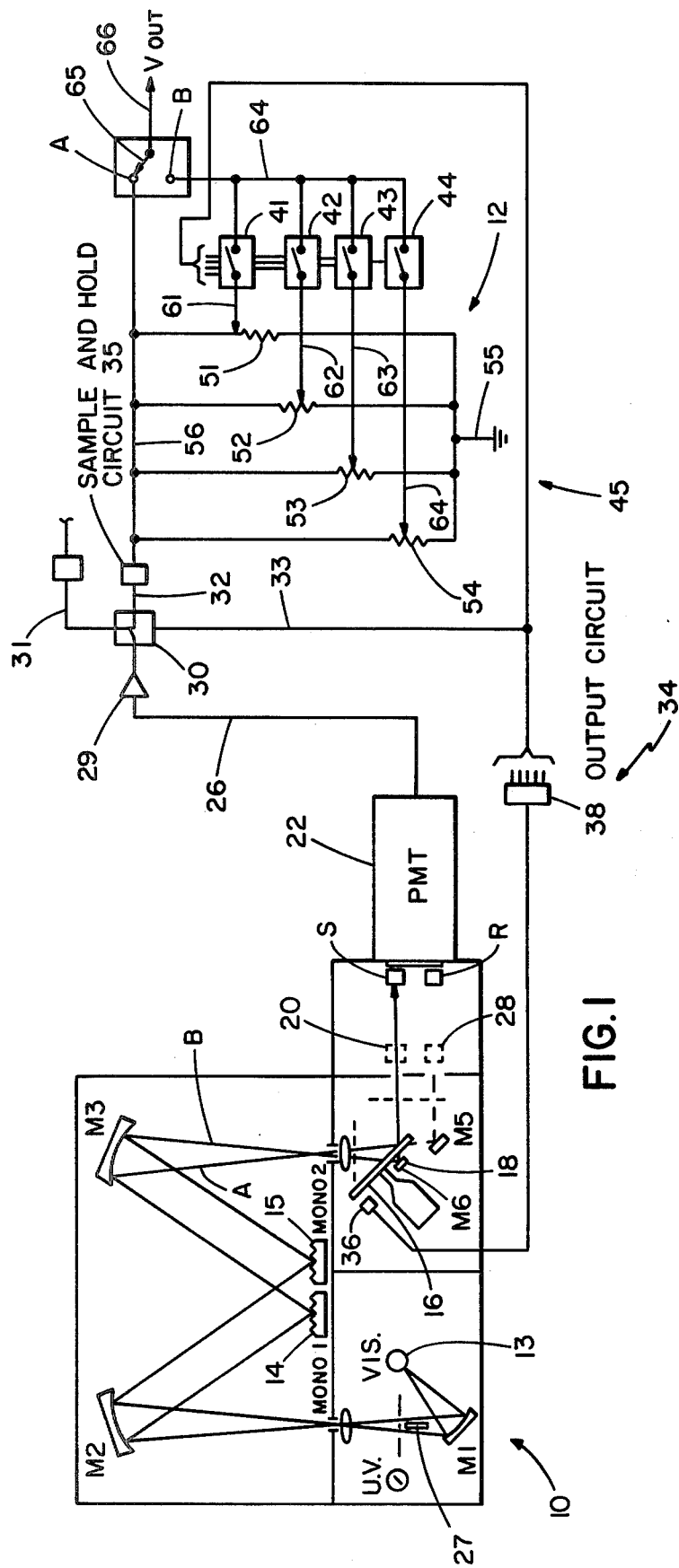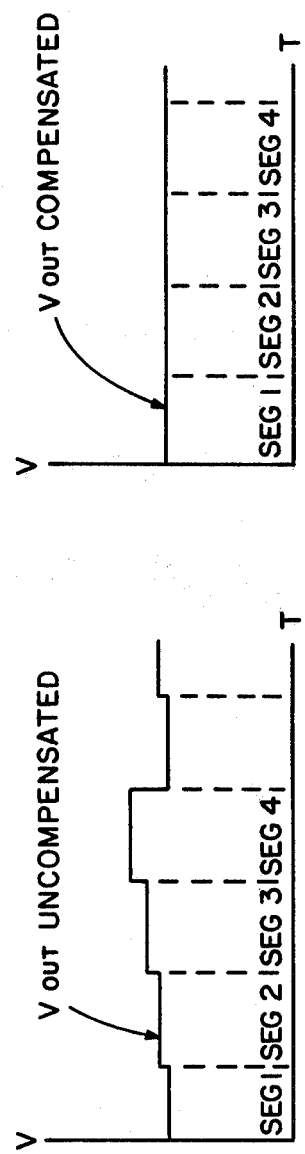
FIG. 1
FIG. 2
FIG. 3

REFLECTIVITY COMPENSATING APPARATUS

BACKGROUND OF THE INVENTION

1. Field of the Invention

The field of the invention is an optical system having apparatus for compensating for differences in reflectivity between two or more reflecting surfaces which reflect the same light to a photodetector.

2. Description of the Prior Art

Heretofore in dual wavelength spectrophotometers where one of two light beams is intermittently reflected by a chopper mirror toward and through a fluid sample to a photodetector, errors are incurred in the measurement of transmittance of light through the sample by reason of the different reflectivities of the mirror segments.

Manufacturers of such spectrophotometers have relied on the supplier of the chopper mirror to match reflectivity among the various mirror segments. With the best matches provided by the suppliers, a difference in reflectivity of 1% is still incurred.

Ideally, the mirror segments should have equal reflectivities so that the electrical signal level produced by a collimated light source reflected by a particular mirror segment and detected by the photodetector will have the same signal level regardless of which segment was reflecting the light to the photodetector. However, manufacturing tolerances result in reflectivity differences among segments of approximately 1 to 2%. These differences produce an undesirable variation in the electrical signal output from the photodetector and errors in the measurement of transmittance of light through a sample situated in the path of the light from the reflecting surface to the photodetector.

As will be described in greater detail hereinafter, the reflectivity compensating apparatus of the present invention provides a sensing device for identifying which of the segments is currently reflecting light from the light source to the photodetector and potentiometers for attenuating the resulting signal levels to a base line signal level produced by the segment which has the lowest reflectivity.

SUMMARY OF THE INVENTION

According to the invention there is provided in an optical system, such as a spectrophotometer, wherein a light beam is reflected by two or more reflecting surfaces to a photodetector and where the reflectivity of each surface varies slightly, the improvement residing in means for compensating for the differences in reflectivity between two or more reflecting surfaces which reflect the same light to a photodetector, said compensating means including impedance means adapted to be coupled to an output signal channel from the photodetector, said impedance means including at least two different impedances, switch means for coupling the impedance to said output signal channel in a manner to attenuate the output signal on the signal channel and control means for synchronously and cyclically operating said switch means to couple sequentially to the output signal channel a particular impedance related to the reflectivity of the reflecting surface from which the signal then on the signal channel was generated so that output signals generated by the same light and reflected by the two or more reflecting surfaces are equal in value.

BRIEF DESCRIPTION OF THE DRAWINGS

FIG. 1 is a schematic diagram of an optical/electrical system utilizing a rotating chopper mirror with mirror segments and utilizing the reflectivity compensating apparatus of the present invention.

FIG. 2 is a graph showing the output voltage on one output signal channel of the system shown in FIG. 1 generated by the light reflected by the mirror segments when the reflectivities of the mirror segments are uncompensated.

FIG. 3 is a graph of the output voltage on the one output signal channel generated by the light reflected by the mirror segments when the reflectivities of the mirror segments are compensated for by the compensating apparatus of the present invention.

DESCRIPTION OF THE PREFERRED EMBODIMENT

Referring now to FIG. 1 in greater detail, there is illustrated schematically therein an optical/electrical system, more specifically a dual wavelength spectrophotometer system, generally identified by reference numeral 10. The system 10 utilizes the reflectivity compensating apparatus of the present invention which is generally identified by reference numeral 12.

The system 10 is of the type which includes a light source 13 which directs light to a system of mirrors including gratings 14 and 15 which refract desired monochromatic light beams that are then directed to a rotating chopper mirror 16 having alternate reflective mirror surfaces and open spaces. The area of the spaces and the mirror segments are equal and in a practical realization of the system 10 a four-segment chopper mirror is utilized.

Each of the optical gratings 14 and 15 refracts a user selected monochromatic light beam A or B which is then reflected to the chopper mirror located behind the rotating mirror 16 and in the path of the light beam B is situated a small stationary mirror 18. In the path of the reflected light beams A and B from either the rotating chopper mirror 16 or the stationary mirror 18 is a transparent sample container 20 having a fluid sample therein and a photodetector 22.

In one use of the dual wavelength spectrophotometer system 10, the light beam A refracted from grating 14 will, when it hits one of the mirror segments of the mirror 16 at an angle of approximately 45°, be reflected through the fluid sample in the sample container 20. Meanwhile, the other light beam B which is refracted by the grating 15 and reflected by a mirror segment will not pass through the sample container 20. Then, when an open space is presented by the chopper mirror 16, the light beam B impinges on the mirror 18 and is reflected by the mirror 18 through the container 20. In this way alternate monochromatic light beams of different wavelengths are passed through the fluid sample in the sample container 20 and the light transmitted through the sample is sensed by the photodetector 22 which then generates an output signal which appears on an output signal channel 26.

In another mode of use, only beam A is utilized and grating 15 is removed or blocked by operation of shutter 27. In this mode, light is also passed to a second transparent container 28. One container, e.g., container 20, contains a sample fluid and the other container, e.g., container 28, contains a reference fluid. When a mirror segment is present in the light path, the light beam A is reflected through container 20. Then, when an open space on the chopper mirror 16 is present in the light path, the light beam A is reflected through container 28.

The output signals on the output channel 26 in either mode of operation are then passed through an amplifier 29 to an analog electrical switch 30 which has two outputs, one being coupled to a reference signal channel 31 and the other being coupled to a sample signal channel 32. The swtich 30 is connected via a conductor 33 to a control apparatus 34 which will be described in greater detail below. Such apparatus senses when a (and which) mirror segment or open space is present in the light path and operates the switch 30 to connect output signal channel 26 to either reference channel 31 or sample channel 32 depending on whether a space or mirror segment is present.

The sample signals on sample channel 32 are then passed to a sample and hold circuit 35. As will be described in greater detail below, the reflectivity compensating apparatus 12 of the present invention is coupled to the output of the sample and hold circuit 35.

Except for the particular control apparatus 34 incorporated into the reflectivity compensating apparatus 12, the foregoing description of the dual wavelength spectrophotometer 10 and its several uses or modes of operation as described above are conventional and form no part of the present invention.

Ideally, the mirror segments of the four-segment chopper mirror 16 should have equal reflectivities so that the electrical signal level produced by a collimated light beam reflected by a particular segment and detected by the photodetector 22 and passed to the sample and hold circuit 35 will have the same signal level regardless of which segment was reflecting the light beam to the photodetector 22. However, manufacturing tolerances result in reflectivity differences among mirror segments of approximately 1 to 2%. These differences produce an undesirable variation and error in the electrical signal level on the sample signal channel 32. This problem is overcome by the reflectivity compensating apparatus 12 of the present invention as will now be described in greater detail below.

As noted above, the reflectivity compensating apparatus 12 includes the control apparatus 34, which in turn, includes a sensing device 36 positioned behind the chopper mirror 16 and in position to sense which mirror segment is 180° from the mirror segment which is reflecting light or if an open space between segments is present. This device 36 can be optical or electrical. For example, the device 36 can be an optical device which includes a light source that directs light toward the backside of the chopper mirror 16. Each segment then has a reflecting surface on the backside thereof which reflects light to a sensor in the device 36 which senses an optical signal when a segment is present or no signal when a segment is not present. This signal is converted by an output circuit 38 to an electrical signal which is transmitted via conductor 33 to switch 30 to connect channel 26 to channel 31 or 32. Also, each segment can have on the backside thereof reflective or non-reflective surfaces which define a binary code of 0, 1, 10 or 11. The optical binary signals reflected are sensed by sensors in the device 36 and directed in the sensing device 36 through appropriate channels to provide a particular optical signal which will energize one of four photodiodes (not shown) in the output circuit 38. That particular photodiode then produces a signal on one of four conductors leading to one of four analog switches 41, 42, 43 or 44 in an attenuation circuit 45.

As shown, the attenuation circuit 45 also includes four variable resistances, actually potentiometers, 51–54 that are coupled between system ground 55 and an output conductor 56 from the sample and hold circuit 35. An adjustable contact 61, 62, 63 or 64 on each potentiometer 51–55 is connected to one of the switches 41–44 which is adapted, when closed, to connect the contact 61, 62, 63 or 64 to one side or position "B" of a switch 65. The switch 65 also has an "A" side or position. In the "A" position, the switch 65 connects the conductor 56 to a signal-out conductor 66 which leads to a comparator (not shown) of the system 10. When in the "B" position, switch 65 connects the switches 41–44 to conductor 66.

In the operation of the apparatus 12, the signal picked up by the sensing device 36 will generate a trigger or control signal in the output circuit 38 which will cause the closing of the appropriate switch 41–44 which is coupled to an impedance, e.g., one of resistances 51–55, which is related to the reflectivity of the mirror segment which is then reflecting light through the sample container 20 and which light is being detected by the photodetector 22 and generates the signal then appearing on conductor 56.

In calibrating or setting the potentiometers 51–54 to compensate for variations in the reflectivity of the four mirror segments of the chopper mirror 16, an operator will first place the switch 65 in the "A" position where the conductor 56 is connected to the conductor 66. Then, while the switch 65 is in the "A" position and the chopper mirror 16 is rotating, a readout, such as a printout, of the Voltage out uncompensated is made as shown in FIG. 2. It is then determined which segment produced which voltage output level and note is made of the segment which produces the lowest output voltage. In the graph of FIG. 2 segment 1 produces the lowest output voltage. Next the related potentiometer, e.g., potentiometer 51, is set at maximum voltage, as shown, and with the switch 65 in the "B" position, each of the remaining potentiometers is adjusted when the related mirror segment is reflecting light to give the same output voltage as that produced when segment 1 is yielding the lowest output voltage, as shown in FIG. 3. This output voltage can be referred to as a base line voltage level. Now switch 65 is left in the "B" position.

From the foregoing description, it will be readily apparent that the reflectivity compensating apparatus 12 of the present invention has a number of advantages, some of which have been described above and others of which are inherent in the invention. The most important advantage, of course, is that differences in reflectivity between mirror segments of a chopper mirror are compensated for whereby undesirable, erroneous readings will be minimized if not altogether eliminated from a spectrophotometer system. Also, obvious variations and modifications can be made to the reflectivity compensating apparatus 12 of the present invention without departing from the teachings of the present invention. Accordingly, the scope of the invention is only to be limited as necessitated by the accompanying claims.

I claim:

1. In an optical system, such as a spectrophotometer, wherein a light beam is reflected by two or more reflecting surfaces to a photodetector and where the reflectivity of each surface varies slightly, the improvement residing in means for compensating for the differences in reflectivity between two or more reflecting surfaces which reflect the same light to a photodetector, said compensating means including impedance means adapted to be coupled to an output signal channel from the photodetector, said impedance means including at least two different impedances, switch means for coupling the impedance to said output signal channel in a manner to attenuate the output signal on the signal channel and control means for synchronously and cyclically operating said switch means to couple sequentially to the output signal channel a particular impedance related to the reflectivity of the reflecting surface from which the signal then on the signal channel was generated so that output signals generated by the same light and reflected by the two or more reflecting surfaces are equal in value.

2. The compensating means according to claim 1 wherein said different impedances are variable resistances.

3. The compensating means according to claim 2 wherein said variable resistances are potentiometers, each of which is connected between the signal channel and system ground and each of which has a variable contact which is connected to said switch means.

4. The compensating means according to claim 3 wherein said switch means comprises a plurality of analog electrical switches equal in number to the number of reflecting surfaces.

5. The compensating means according to claim 4 wherein said compensating means includes a two-position calibrating switch coupled to said switches, to the output signal channel and to a signal-out conductor and operable in one position to connect the output signal channel to said signal-out conductor and, in a second or operating position, to connect said switches to said signal-out conductor where operation of said control means to selectively close the appropriate switch results in the attenuation of the signal on the output signal channel to a base line signal level which then appears on the signal-out conductor and results in the output signal on the signal-out conductor remaining constant for the same light reflected by the different reflecting surfaces.

6. A dual wavelength spectrophotometer comprising a rotating segmented mirror having an equal number of mirror segments and open spaces of equal area, a light source operable to direct light toward the rotating mirror segments, a photodetector positioned to receive light reflected from the mirror segments, an output signal channel from the photodetector, impedance means comprising a plurality of impedances equal in number to said mirror segments and adapted to be coupled to said output signal channel, switch means for coupling said impedances to said output signal channel, control means for sensing and identifying which mirror segment is reflecting light and for selectively operating said switch means to couple the appropriate impedance related to the reflectivity of that mirror segment to the signal output channel to attenuate the signal generated by light reflected from that mirror segment and received by the photodetector to a base line signal level, each of the other impedances being chosen so as to attenuate the signal generated by light received by the photodetector from a particular mirror segment to said base line signal level thereby to compensate for differences in reflectivity of the mirror segments.

7. A dual wavelength spectrophotometer comprising a light source, a rotatable chopper mirror having alternating mirror segments and open spaces of equal area positioned in the path of light from said light source, a photodetector positioned to receive light reflected by each mirror segment as it cuts through a path of light from said light source, a sample container positioned in the path of the reflected light, said photodetector being positioned to receive light which is not only reflected by the mirror segments but which is also transmitted through a fluid sample in the sample container, a signal output channel from said photodetector, impedance means adapted to be coupled to said signal output channel and comprising a plurality of impedances equal in number to, and related to, said mirror segments, switch means for selectively coupling each impedance to the signal output channel, and control means for controlling the operation of said switch means and including sensing means for sensing which mirror segment is reflecting light and for operating said switch means in response thereto to couple an appropriate impedance related to the reflectivity of that mirror segment to said signal channel to attenuate the signal generated by the light received by the photodetector from that mirror segment to a base line signal level and each of the other impedances also being related to the reflectivity of one of said mirror segments so that when such impedance is coupled to said output signal channel it attenuates an output signal generated in the photodetector by light reflected by a related one of said mirror segments to the base line signal level so that differences in the reflectivity of each mirror segment are compensated for thereby to reduce, if not altogether eliminate, error in the measurements of light transmitted through the fluid sample.

* * * * *